(12) United States Patent
Pham et al.

(10) Patent No.: US 7,347,130 B2
(45) Date of Patent: Mar. 25, 2008

(54) APPARATUS AND METHOD FOR CUTTING SPINAL IMPLANTS

(75) Inventors: Tan-Loc Pham, Talence (FR); Francois Paponneau, Gradignan (FR); Cedric De Conninck, Cesta-Gazinet (FR); Jerome Despiau, Lacanau de Mios (FR)

(73) Assignee: Stryker Spine (FR)

( * ) Notice: Subject to any disclaimer, the term of this patent is extended or adjusted under 35 U.S.C. 154(b) by 134 days.

(21) Appl. No.: 10/808,817

(22) Filed: Mar. 25, 2004

(65) Prior Publication Data

US 2005/0125986 A1    Jun. 16, 2005

(30) Foreign Application Priority Data

Dec. 16, 2003    (EP) ................................. 03293189

(51) Int. Cl.
B23B 3/26    (2006.01)
(52) U.S. Cl. .......................................... 82/101; 82/110
(58) Field of Classification Search .................. 82/101, 82/110, 117; 29/27 C, 26 B, 27 R
See application file for complete search history.

(56) References Cited

U.S. PATENT DOCUMENTS

| | | | | |
|---|---|---|---|---|
| 2,125,178 A | * | 7/1938 | Ullmer | 148/201 |
| 3,073,193 A | * | 1/1963 | Grant | 82/117 |
| 3,363,491 A | * | 1/1968 | George | 82/110 |
| 3,748,934 A | | 7/1973 | Lezberg | |
| 4,057,893 A | * | 11/1977 | Smith et al. | 29/560 |
| 5,702,449 A | | 12/1997 | Mckay | |
| 6,096,081 A | | 8/2000 | Grivas et al. | |
| 6,344,057 B1 | | 2/2002 | Rabbe et al. | |
| 6,442,814 B1 | | 9/2002 | Wagner et al. | |
| 6,557,226 B1 | * | 5/2003 | Landry et al. | 29/27 C |

FOREIGN PATENT DOCUMENTS

| | | |
|---|---|---|
| DE | 173 215 C | 7/1906 |
| EP | 0 129 531 A | 12/1984 |
| JP | 60-120042 A | 6/1985 |

* cited by examiner

Primary Examiner—Willmon Fridie, Jr.
(74) Attorney, Agent, or Firm—Lerner, David, Littenberg, Krumholz & Mentlik, LLP

(57) ABSTRACT

An apparatus and method for cutting spinal implants to a desired length is disclosed. The spinal implant is supported on a mandrel that rotates while a cutting blade cuts the spinal implant. The apparatus and method accurately size and cut spinal implants to the desired length.

33 Claims, 13 Drawing Sheets

APPARATUS AND METHOD FOR CUTTING SPINAL IMPLANTS

CROSS-REFERENCE TO RELATED APPLICATIONS

The present application claims priority of French application No. 03293189.1 which was filed on Dec. 16, 2003.

FIELD OF THE INVENTION

The invention relates to spinal implants, and in particular, methods and apparatus for cutting spinal implants.

BACKGROUND OF THE INVENTION

The spinal column is a highly complex system of bones and connective tissues that provides support for the body and protects the delicate spinal cord and nerves. The spinal column includes a series of stacked vertebral bodies, each vertebral body including an inner or central portion of relatively weak cancellous bone and an outer portion of relatively strong cortical bone. Situated between each vertebral body is an intervertebral disc that cushions and dampens compressive forces exerted upon the spinal column. A vertebral canal containing the spinal cord and nerves is located behind the vertebral bodies.

A surgical technique commonly referred to as spinal fixation uses surgical implants for fusing together and/or mechanically immobilizing two or more vertebral bodies of the spinal column. Spinal fixation may also be used to alter the alignment of adjacent vertebral bodies relative to one another to change the overall alignment of the spinal column. Such techniques have been used effectively to treat a wide variety of conditions and, in most cases, to relieve pain.

One spinal fixation technique involves the fusion of adjacent bone structures. Conventional procedures for a fusion procedure include partial or total excision of an injured disc portion, e.g., discectomy, and replacement of the excised disc with biologically acceptable plugs or bone wedges. The plugs are placed between adjacent vertebrae to maintain normal intervertebral spacing and to achieve, over a period of time, bony ingrowth or "fusion" with the plug and opposed vertebrae.

Alternatively, a fusion cage may be inserted within a tapped bore or channel formed in the intervertebral space to stabilize the vertebrae and maintain a pre-defined intervertebral space. A pair of fusion cages may also be implanted within the intervertebral space. After a period of time, the soft cancellous bone of the surrounding vertebral bone structures infiltrates the cage through a series of apertures in the cage wall and unites with bone growth inducing substances disposed within an internal cavity of the cage wall to eventually form a solid fusion of the adjacent vertebrae.

Presently existing fusion cages are sized to fit between adjacent vertebrae by cutting the cage to adjust the length of the cage. The length of the cage may also be adjusted by providing end caps, the position of which can be adjusted to alter the overall length of the cage. For example, U.S. Pat. No. 6,344,057 describes a cylindrical fusion implant that has an adjustable length in that threaded end caps can be adjusted telescopically with respect to the cage. With regards to cutting fusion cages, there does not appear to be any convenient method and apparatus for quickly and accurately measuring and cutting the length of a fusion cage. Typically, a surgeon will use a caliper or other measuring device to determine the appropriate length of the spinal implant to fit in an intervertebral space, but there is no convenient way to transfer this measurement to a cutting device to make an accurate cut based on the intervertebral spacing measured by the caliper. It would be desirable to provide improved apparatus and methods for measuring and cutting spinal implants such as fusion cages to a desired length.

SUMMARY OF THE INVENTION

In accordance with one or more embodiments of the present invention, a spinal implant cutting apparatus is provided. According to one embodiment, the apparatus comprises a first mandrel configured to support a moveable blade from a first position at which it is spaced from the spinal implant supported on the first mandrel and a second position at which it is in cutting engagement with the spinal implant. In one embodiment, the spinal implant is configured to be rotated with respect to the cutting blade. The first mandrel is configured to support a hollow spinal implant such that the spinal implant is slidably mounted on the first mandrel. As used herein, the term mandrel is not limited to mandrels that are cylindrical, and any shaped mandrel can be used to support the hollow spinal implant during cutting of the implant. In certain embodiments, the first mandrel is detachable from the apparatus to permit loading and removal of the spinal implant on the first mandrel.

According to one or more embodiments, the mandrel is preferably rotatable about an axis, and means are provided for rotating the mandrel. Rotation of the mandrel can be accomplished by providing a handle associated with the first mandrel configured to rotate the first mandrel. According to certain embodiments, the handle may further include a ratchet mechanism to facilitate rotation of the first mandrel.

In certain embodiments, the apparatus comprises a frame, and the cutting blade is part of a cutting fixture that is slidably mounted on the frame. In some embodiments, a first reference point is associated with the frame and a second reference point is associated with the cutting fixture. The reference points are preferably configured to permit placement of the cutting blade such that the spinal implant can be cut to a desired length. The reference points may comprise any convenient shape such as a pair of notches, slots, holes, indentation or the like configured to receive ends of an intervertebral caliper measurement device. In some embodiments, a plurality of reference points such as notches may be associated with the cutting fixture referenced to a plurality of different sized spinal implants.

According to certain embodiments, the cutting blade is readily removable from the cutting fixture. In such embodiments, the cutting blade is held in place by a locking spring. In one or more embodiments, the cutting blade is configured to be positioned at a plurality of positions along the length of the spinal implant. In certain embodiments, the cutting fixture is mounted on a frame configured to permit the cutting blade to move in increments with respect to the spinal fixture. In such embodiments, the increments may be matched to marked spacings associated with the spinal implant. In certain preferred embodiments, the cutting blade fixture is movable in a direction substantially transverse to the longitudinal axis of the spinal implant. In these embodiments, an adjustment knob can be provided for this purpose, and rotation of the adjustment knob causes movement of the cutting blade substantially transverse to the longitudinal axis of the spinal implant.

Another embodiment relates to a spinal implant cutting apparatus comprising a frame including a rotatable first mandrel for supporting a substantially cylindrical spinal implant and a cutting fixture including a cutting blade, the cutting fixture slidably mounted to the frame such that the cutting fixture can be moved to a plurality of positions along the length of the spinal implant and cut the spinal implant to a preselected length. In certain embodiments, the apparatus may further comprise indicia associated with the apparatus for receiving an intervertebral space measurement to accurately determine the length of the spinal implant. According to one or more embodiments, the spinal implant includes a substantially tubular cage.

In other embodiments of the invention, a spinal implant cutting apparatus is provided which comprises a first mandrel removably attached to a frame, the removable mandrel adapted to receive a substantially tubular spinal implant, a cutting blade configured to be placed in cutting engagement with the spinal implant, and reference marks associated with the cutting blade and the apparatus are adapted to receive an intervertebral spacing measurement from a caliper.

Still other embodiments of the invention relate to a method of sizing a spinal implant comprising using a measurement device to obtain the distance between two vertebrae to obtain a desired length for the spinal implant, mounting the spinal implant on a mandrel associated with a cutting apparatus including a cutting fixture mounted to a frame, the cutting fixture including a cutting blade, securing the mandrel to the cutting apparatus, positioning the cutting blade with respect to the spinal implant with reference to the distance obtained by the measurement device, and cutting the spinal implant to the desired length. According to certain method embodiments, positioning the cutting blade includes sliding the cutting fixture with respect to the spinal implant. The method may further comprise locking the cutting fixture in place. In preferred embodiments, the measurement device includes a caliper having a pair of arms. In certain embodiments, the apparatus includes a pair of reference marks associated with the ends of the spinal implant after it has been cut. In certain embodiments in which calipers are used as the measurement device, the spacing between the arms of the caliper corresponds to the desired length of the spinal implant. According to some embodiments, the method may further include placing the arms adjacent the reference marks to position the cutting blade for cutting the spinal implant to the desired length.

In one or more embodiments of the method of the invention, the cutting blade is advanced towards the spinal implant so that the cutting blade and the spinal implant are in contact, and the mandrel is rotated until the blade cuts through the spinal implant. After the spinal implant has been cut, the cutting blade is moved away from the spinal implant. Thereafter, according to certain embodiments, the first mandrel can be removed from the apparatus after the spinal implant has been cut, and the cut spinal implant is removed from the first mandrel.

According to other embodiments of the invention, a method of sizing a substantially cylindrical hollow spinal implant is provided comprising sliding the spinal implant on to a mandrel, measuring the size of the implant needed using a caliper having a pair of arms, the size of the implant corresponding to the distance between the arms, positioning a caliper with respect to the spinal implant and the cutting blade to determine the length of the implant to be cut, fixing the position of the cutting blade in relation to the spinal implant, and rotating the mandrel while the blade is in contact with the spinal implant until the cutting blade has cut through the spinal implant. In some embodiments, the spinal implant includes a spinal cage. According to one or more embodiments, the spinal cage includes circumferential grooves formed on the exterior surface of the cage and spaced along the length of the cage. In certain embodiments, the cutting blade is associated with a track and the blade can be moved in increments corresponding to the spacing between the circumferential grooves on the cage. In embodiments that include end pieces or end caps as part of a spinal cage assembly, the length of the cage will be adjusted to include the height of the end pieces. Thus, when a pair of calipers is used to measure the space between two vertebra, the size of the total implant will include the length of the cage plus the height of the cage.

BRIEF DESCRIPTION OF THE DRAWINGS

A more complete appreciation of the subject matter of the present invention and the various advantages thereof can be realized by reference to the following detailed description in which reference is made to the accompanying drawings in which.

DETAILED DESCRIPTION OF THE PREFERRED EMBODIMENTS

Before describing several exemplary embodiments of the invention, it is to be understood that the invention is not limited to the details of construction or process steps set forth in the following description. The invention is capable of other embodiments and of being practiced or carried out in various ways.

Figure 1:
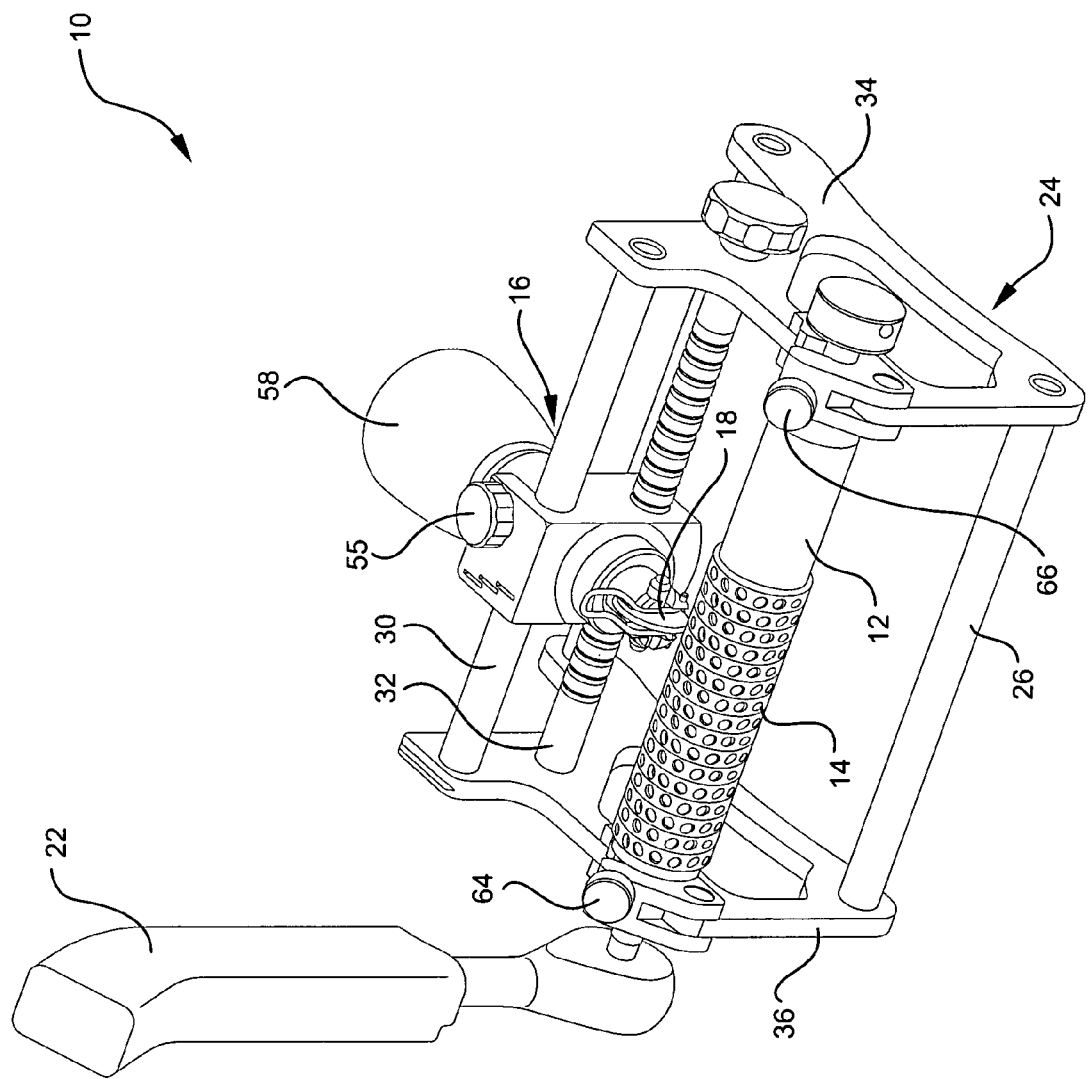
FIG. 1 is a perspective view of an assembled spinal implant cutting apparatus according to one or more embodiments of the present invention showing the spine implant holding a mandrel removed from the apparatus.

Referring now to the drawings and particularly to FIG. 1, one or more embodiments of the invention relate to a spinal implant cutting apparatus 10. The apparatus includes at least a first mandrel 12 configured to support a substantially cylindrical spinal implant 14. A cutting blade fixture 16 is mounted to the apparatus and configured to maintain a cutting blade 18 in a spaced apart relationship from the first mandrel 12. As will be described in more detail below, the cutting blade 18 can be positioned with respect to the first mandrel 12 to be in cutting engagement with the spinal implant 14 and to accurately cut the spinal implant 14 to a desired length.

Figure 2:
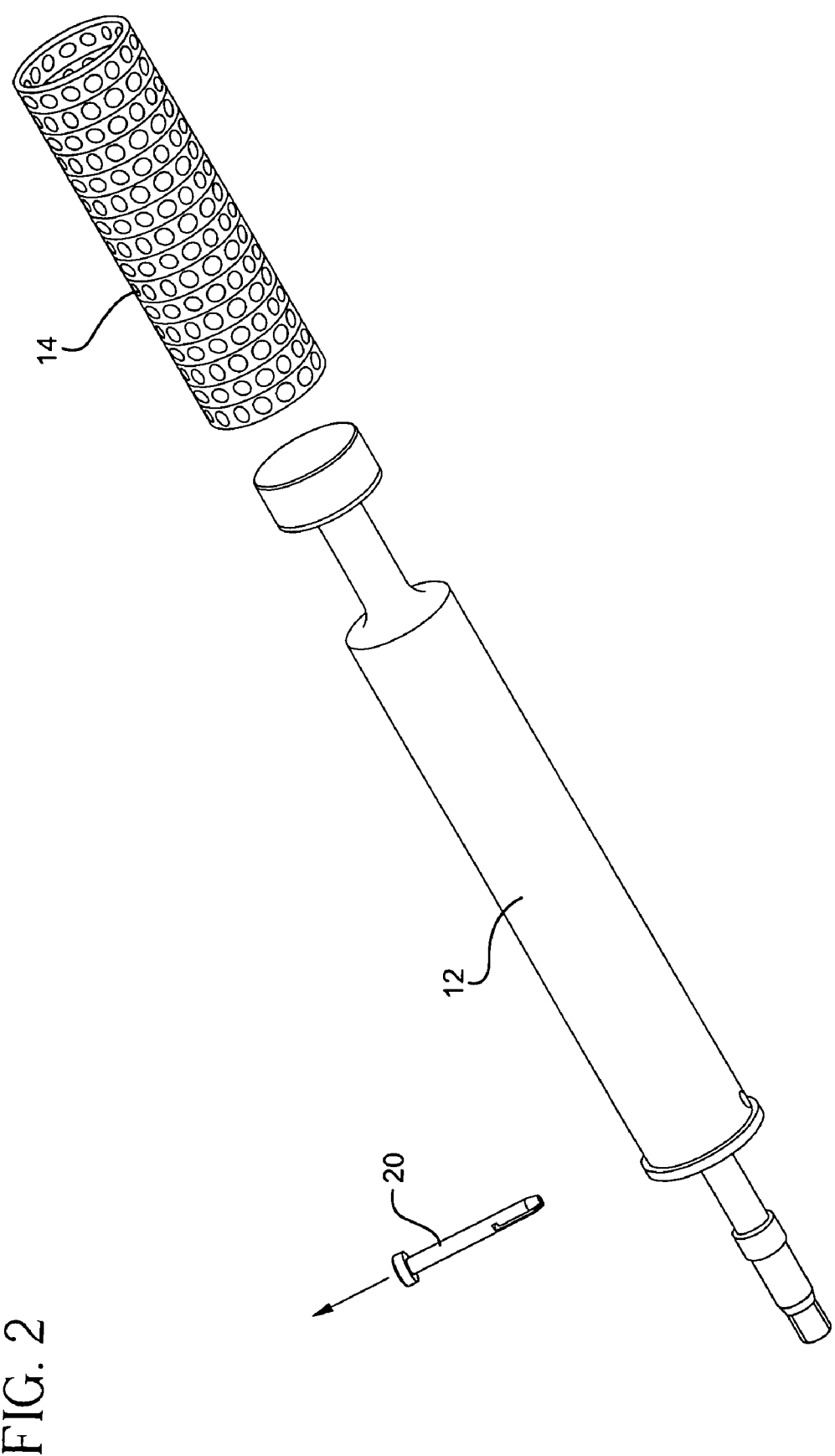
FIG. 2 is a perspective view showing a spinal implant being loaded onto a mandrel of a cutting apparatus according to one ore more embodiments of the present invention.
Figure 3:
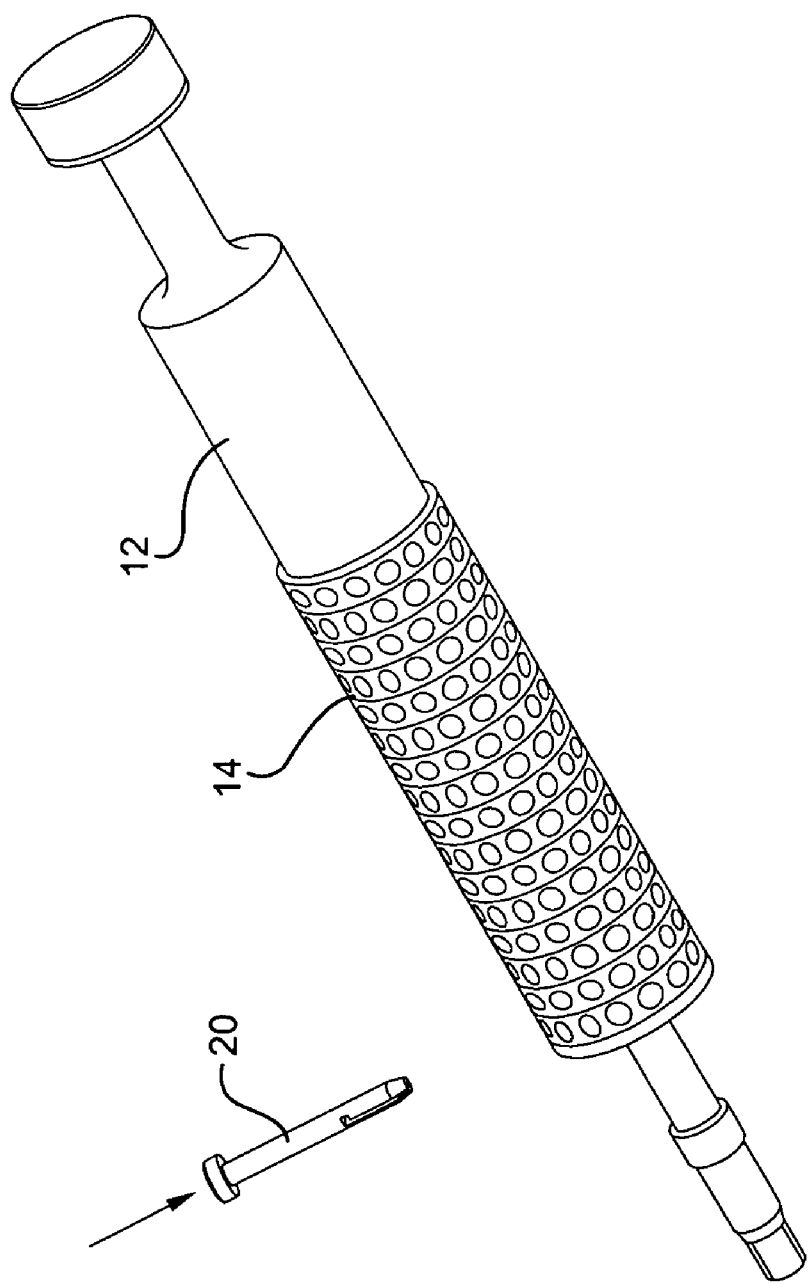
FIG. 3 is a perspective view showing a spinal implant mounted on a mandrel of a cutting apparatus according to one or more embodiments of the present invention.

As shown in FIG. 1, the spinal implant 14 mounted to the mandrel 12 is configured to be rotated with respect to the cutting blade 18. Although the mandrel 12 is shown in the Figures as being cylindrical in shape, it will be understood that the mandrel could have other shapes to support hollow spinal implants during cutting operations. For example, the cross-sectional shape of the mandrel 12 could be triangular, square, hexagonal, or other shapes. In addition, mandrel 12 does not have to be a continuous mandrel as shown in the Figures. A pair of mandrels could be used to support the end portions of the spinal implant 14. Referring now to FIG. 2, the first mandrel 12 is configured to support a hollow spinal implant 14 such that the spinal implant 14 is slidably mounted on the first mandrel 12. A pin 20 or other suitable holding element to hold the spinal implant 14 on the mandrel 12 when the implant is being cut. FIG. 3 shows the spinal implant 14 mounted on the mandrel 12 and the pin 20 as it is being placed to secure the implant 14 to the first mandrel 12.

Figure 4:
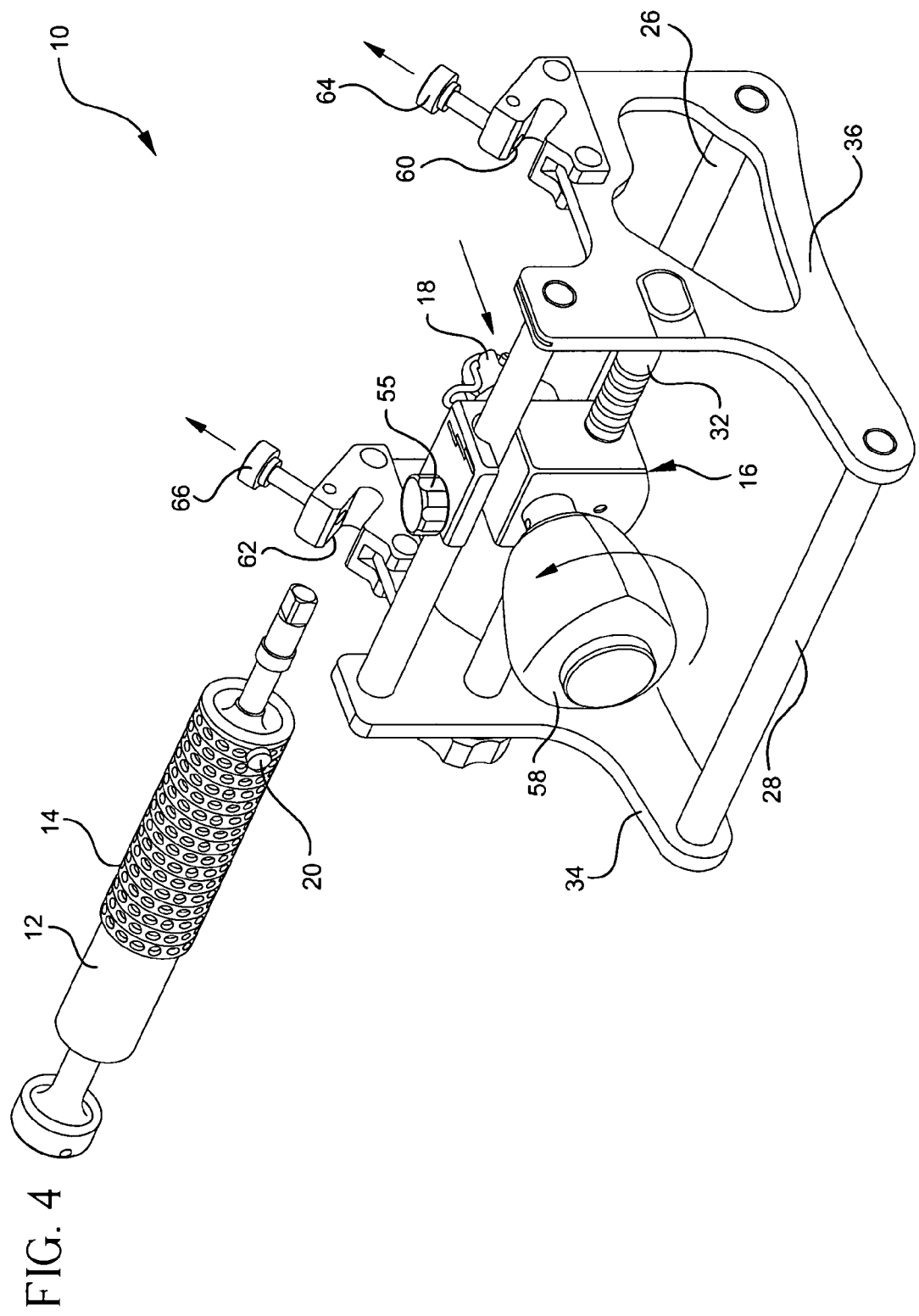
FIG. 4 is a side perspective view showing a mandrel being mounted to a cutting apparatus according to one or more embodiments of the present invention.

As shown in FIG. 4, the first mandrel 12 is detachable from the apparatus to permit loading and removal of the spinal implant 14 on the first mandrel 12. Referring again to FIG. 1, in preferred embodiments, the apparatus 10 includes means for rotating the first mandrel 12. In the embodiment shown in the Figures, and in particular FIG. 1, a handle 22 is provided for rotating the first mandrel 12. Preferably, the handle 22 has a ratchet mechanism (not shown) associated with the handle for rotating the first mandrel 12. Ratchet mechanisms are known in the art, and a person skilled in the art can select an appropriate ratchet mechanism for rotating the first mandrel 12. In use, the handle 22 can be moved in a back and forth (e.g., forward and backward or up and down) motion to cause the first mandrel 12 and the spinal implant 14 mounted thereon during the cutting operation, which will be described in more detail below. It will be understood that other devices can be used to rotate the first mandrel 12. For example, the first mandrel 12 could be driven by a knob or crank attached to the end of the first mandrel 12, or alternatively, the first mandrel 12 could be rotated by a motor or other drive mechanism attached to the first mandrel 12.

In the embodiment shown in the Figures, the cutting apparatus 10 includes a frame 24 which may include one or more mandrels including the first mandrel 12. In one or more embodiments, the cutting fixture 16 is slidably mounted to the frame 24. In particular the frame 24, may include a pair of support rods 26, 28. The apparatus 10 may further include a pair of mounting rods 30, 32 for mounting the cutting fixture 16 to the frame 24. The frame 24 may further include a pair of end members 34, 36, and the mandrel 12, and rods 26, 28, 30, 32 extend between the end members 34, 36.

Figure 6:
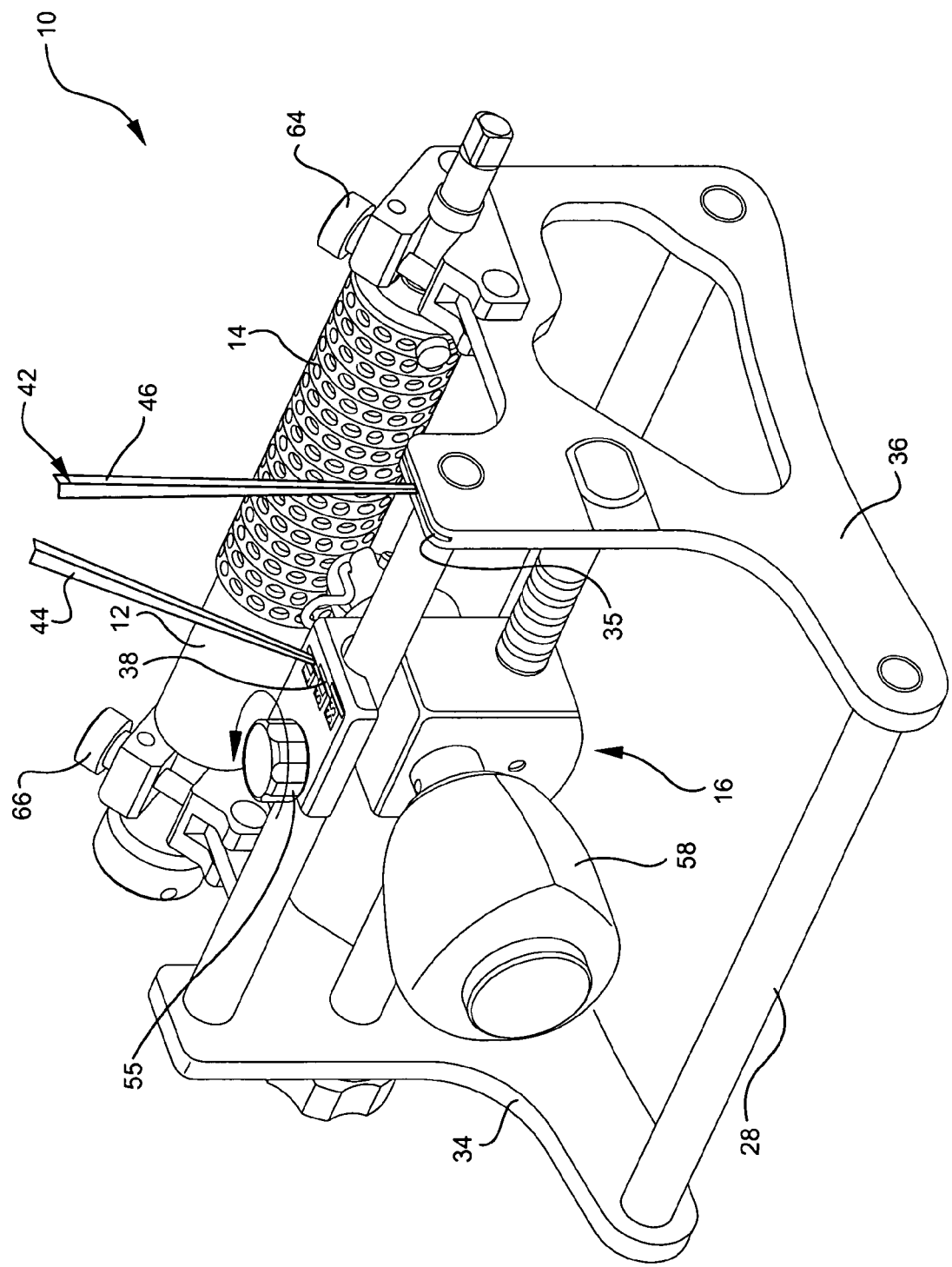
FIG. 6 is a rear perspective view showing the cutting blade being positioned using a caliper measurement according to one or more embodiments of the present invention.
Figure 7:
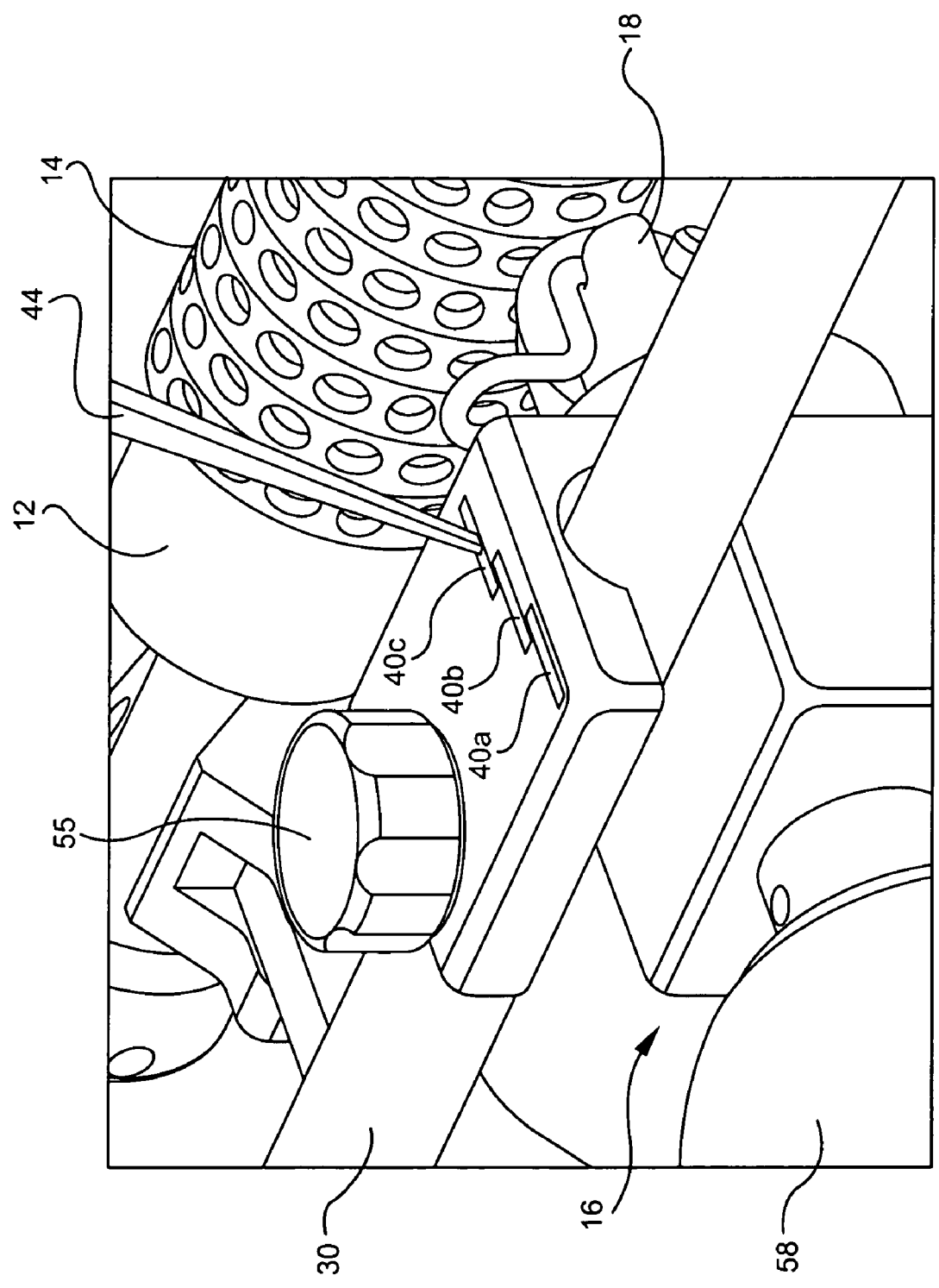
FIG. 7 is an enlarged perspective view showing indicia on a cutting fixture of the cutting apparatus according to one or more embodiments of the present invention.

According to one or more embodiments, and as best shown in FIGS. 6 and 7, the apparatus 10 may further comprise a first reference point 38 associated with the frame 24, and in particular end member 36 and a second reference point 40 associated with the cutting fixture 16. As will be described in more detail below, the reference points 38, 40 are configured to permit placement of the cutting blade 18 such that the spinal implant 14 can be cut to a desired length. The reference points 38, 40 can be in any form suitable for the purpose of accurately referencing the length of the spinal implant 14 to be cut, and may be in the form of indicia, indentations, markings, holes, or notches. In the embodiment shown in the Figures, the reference points 38, 40 comprise a pair of notches configured to receive ends of an intervertebral caliper measurement device 42. The caliper 42 includes a pair of arms 44, 46, which can be used to obtain the distance between two vertebrae into which the spinal implant 14 is inserted after it has been cut to the desired size. In preferred embodiments, a plurality of notches 40a, 40b, 40c are provided on the cutting fixture 16, each of the notches 40a, 40b, 40c may be referenced to a different sized spinal implant or spinal implant accessory such as an end cap for a spinal cage implant.

Figure 13:
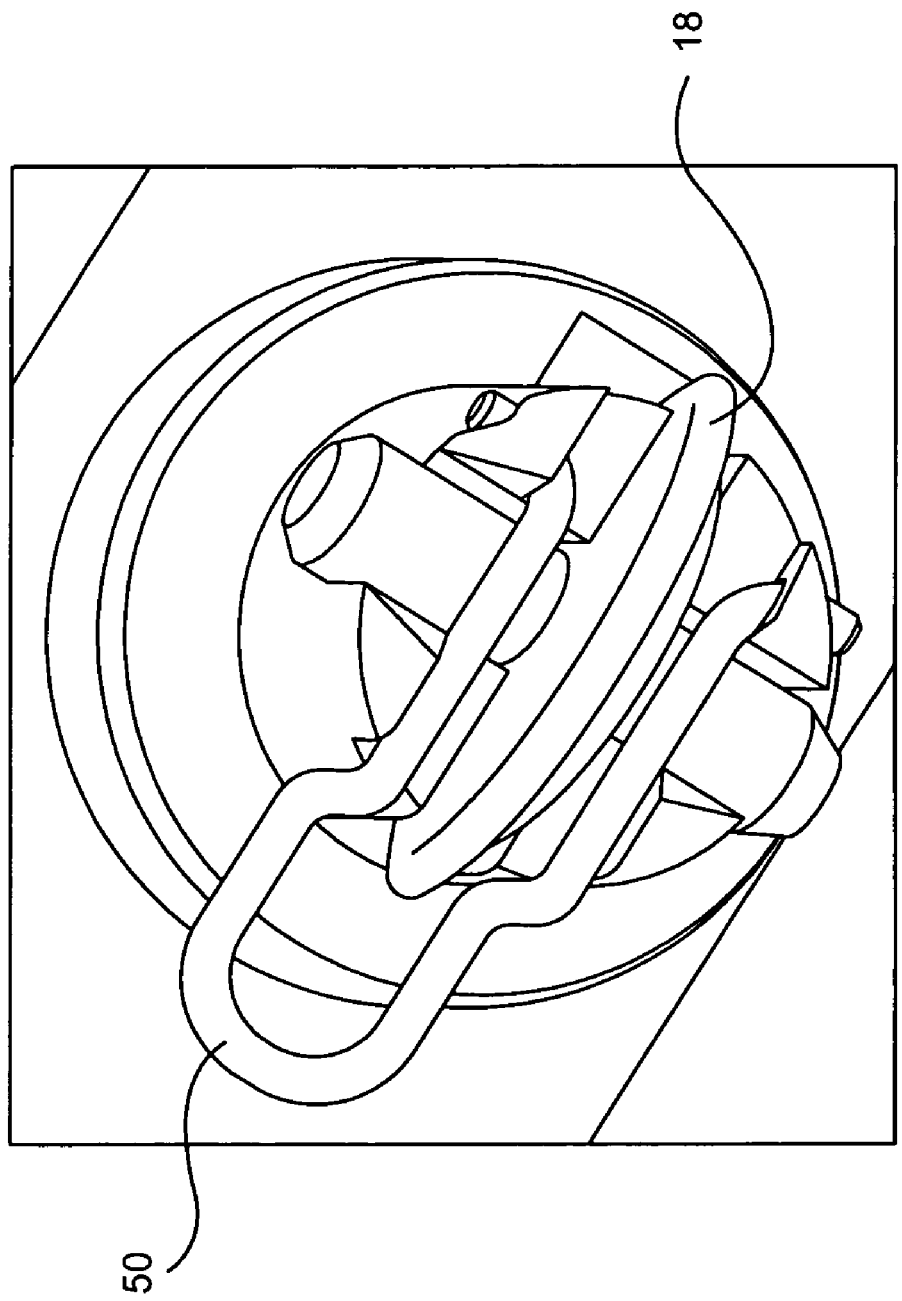
FIG. 13 is a bottom view of a blade used with a cutting apparatus according to one or more embodiments.

Referring now to FIG. 13, according to one or more embodiments, the cutting blade 18 is readily removable from the cutting blade fixture 16. The cutting blade 18 may be held in place by a locking spring 50, which can be quickly moved between a locked and unlocked position to change the blade.

According to one or more embodiments, the cutting blade fixture 16 and cutting blade 18 are configured to be positioned at a plurality of positions along the length of the spinal implant. The cutting blade fixture 16 can be mounted to the frame, and in particular on the mounting mandrels 30, 32. The mounting mandrel 32 may include indicia, for example, grooves 52 providing cutting increments 54 thereon. In preferred embodiments, the increments 54 on the mandrel 32 are matched to marked spacings or increments associated with the spinal implant. A locking knob 55 is provided on the cutting blade fixture 16 to lock and release the cutting blade fixture on the mounting mandrel 30.

Figure 9:
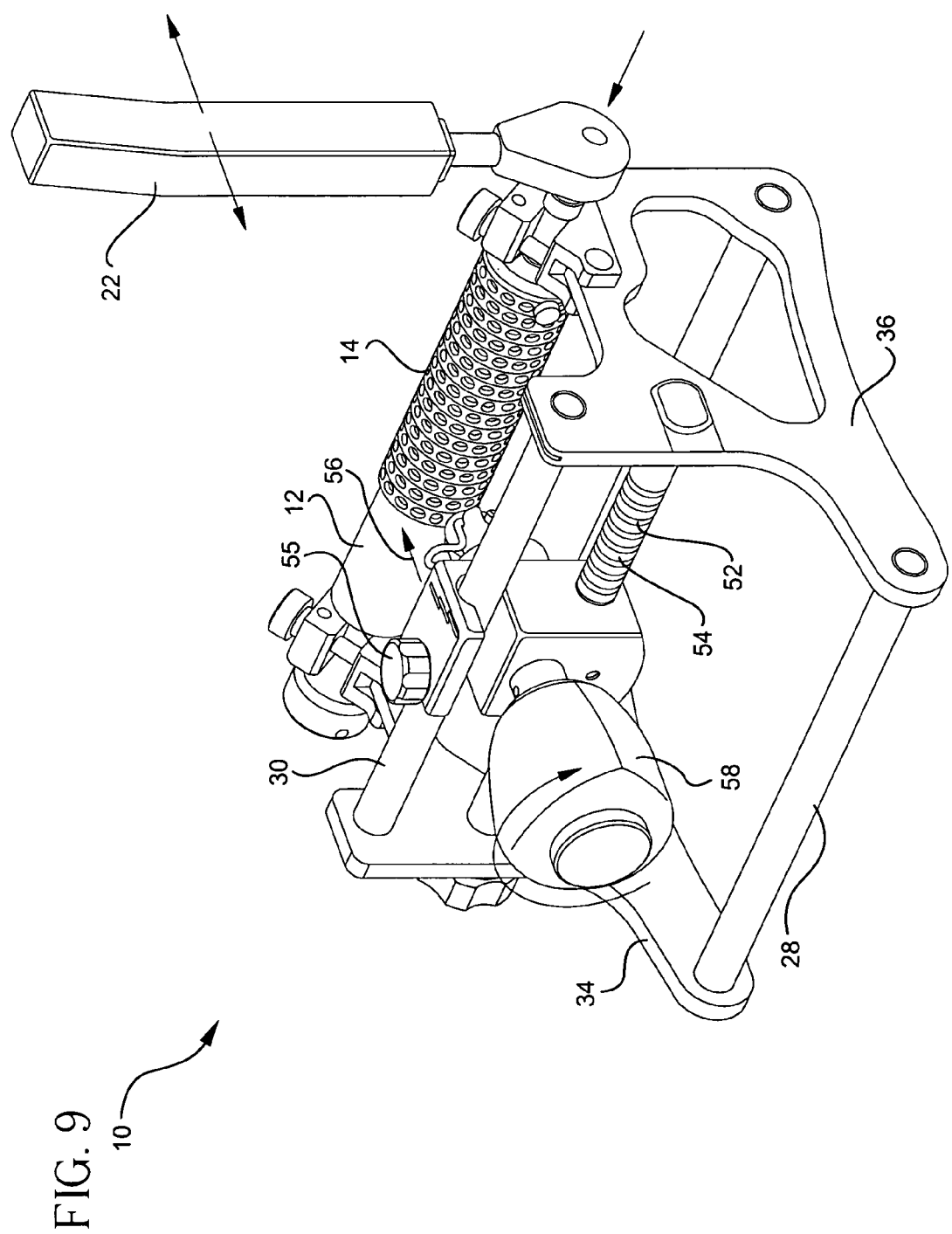
FIG. 9 is a perspective view showing the operation of the cutting apparatus according to one or more embodiments.

According to one or more embodiments of the invention and with reference to FIG. 9, the cutting blade fixture 16 and cutting blade 18 are movable in a direction substantially transverse to the longitudinal axis of the spinal implant 14, as indicated by arrow 56. The cutting blade fixture 16 may include an adjustment knob 58 or other suitable device that causes movement of the cutting blade 18 in the direction 56 substantially transverse to the longitudinal axis of the spinal implant. The adjustment knob 58 may be attached to a first end of threaded shaft (not shown), and the cutting blade 18 can be attached to the other end of the threaded shaft, and rotation of the knob 58 causes movement of the cutting blade fixture.

One or more embodiments of the invention relates to a method of sizing a spinal implant. In use, a practitioner, for example, an orthopaedic surgeon can conveniently use the cutting apparatus 10 described herein during a procedure involving the insertion of a spinal implant such as a spinal cage between two vertebrae. The apparatus of the present invention is particularly well-suited for cutting corpectomy cages, but the apparatus could also be adapted for cutting other types of substantially cylindrical spinal implants. Corpectomy cages are known in the art, and they typically comprise a central, substantially cylindrical body having a hollow interior. The apparatus 10 of the present invention is particularly useful for cutting corpectomy cages having an array of grooves spaced along the length of the cage that each circumscribe the outer circumference of the substantially cylindrical body. Corpectomy cages typically are used with end caps that are attached to each end of the substantially cylindrical body. The end plates are relatively flat structures with a central opening. The end plates can have different sizes to and angulations. Spinal implants are typically made of a biologically inert material, for example, any metal customarily used for surgical devices such as titanium or stainless steel. The invention is not limited to any particular material.

Because the mandrel 12 can be removably mounted to the apparatus 10, different diameter mandrels can be used to support different diameter cages. As a non-limiting example, mandrels can be provided adapted to support 10 mm, 12 mm, 14 mm, 16 mm, 20 mm and 25 mm diameter cages having lengths between 10 mm and 120 mm. It will be understood, however, that the invention is not limited to cutting a spinal implant of any specific diameter or length. The apparatus 10 allows a practitioner to rapidly and easily transfer the measurement of the space between two vertebrae taken by the caliper to the cutting apparatus 10 so that the apparatus can quickly and easily cut the spinal implant.

Therefore, in use, a practitioner uses a measurement device such as a caliper to obtain the distance between two vertebrae to obtain a desired length for the spinal implant. Referring to FIGS. 1 and 2, an uncut spinal implant 14 is then mounted on a mandrel 12 associated with a cutting apparatus 10 including a cutting fixture 16 mounted to a frame 24, the cutting fixture including a cutting blade 18. In FIG. 2, the spinal implant 14 is in the form of a substantially cylindrical and hollow corpectomy cage, and the hollow cage is mounted to the mandrel 12 by sliding the cage over the mandrel 12. Referring to FIG. 3, a pin 20 or other suitable holding device can be used to hold the spinal implant 14 on the mandrel 12. The holding structure or pin 20 can be inserted in one of a plurality of openings or holes contained in the spinal implant.

Figure 5:
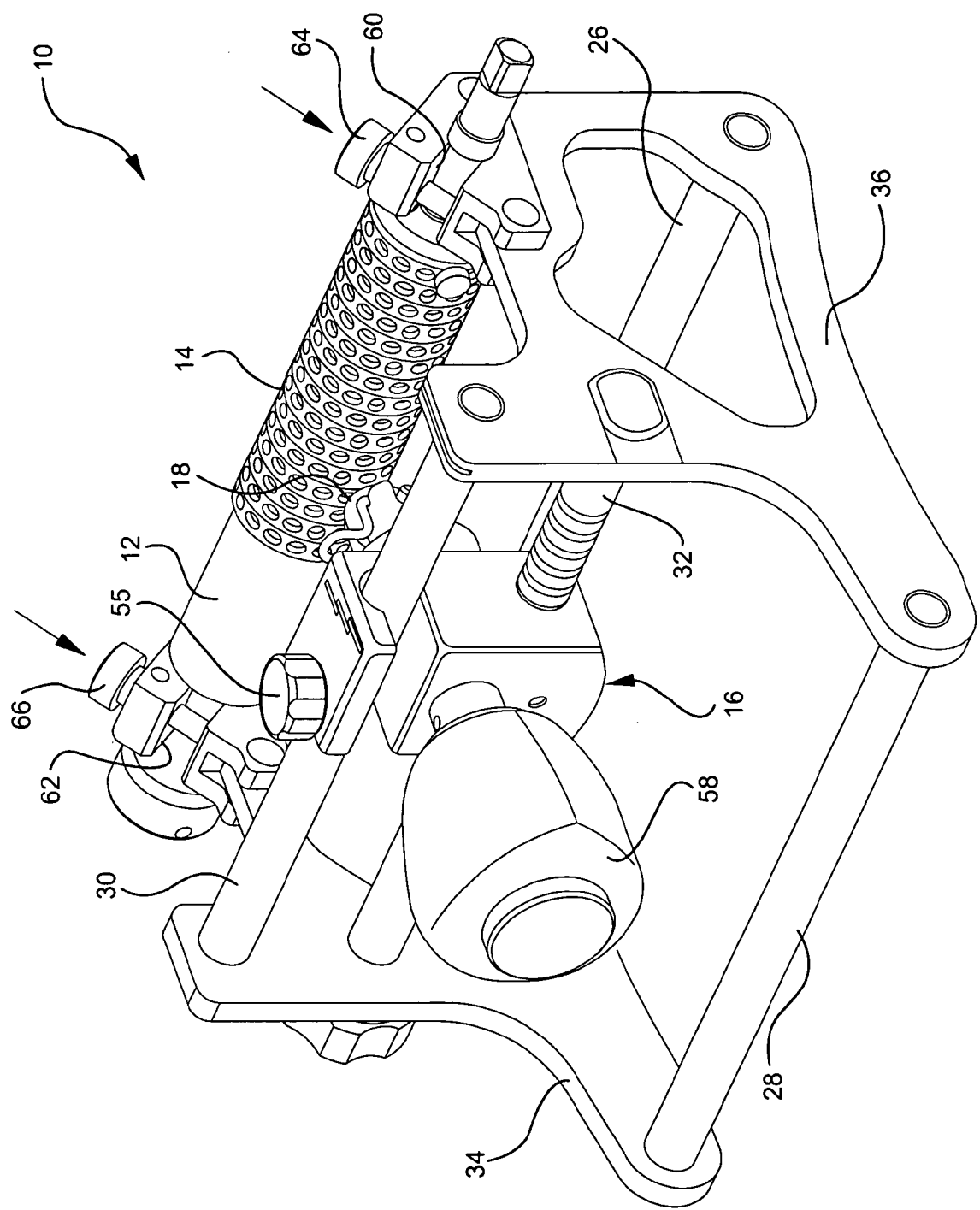
FIG. 5 is a side perspective view showing the mandrel mounted to the cutting apparatus according to one or more embodiments of the present invention.

Referring now to FIGS. 4 and 5, after the spinal implant 14 has been mounted to the mandrel 12, the mandrel is secured to the cutting apparatus. The end members 34, 36 may include channels 60, 62 formed therein or separate brackets including channels for receiving the mandrel 12. The channels may be made from, or include inserts made from a friction reducing material such as plastic, for example PTFE or PEEK. A pair of thumbscrews 64, 66 or other suitable holding devices secure the mandrel 12 to the cutting apparatus 10. Other suitable holding devices include, but are not limited to, clips and holding pins. After the mandrel 12 has been secured to the apparatus 10, the cutting blade 18 is positioned with respect to the spinal implant 14 with reference to the distance obtained by the measurement device. As shown in FIGS. 6 and 7, the calipers which have obtained the desired length of the spinal implant are inserted into the reference points 38, 40 while the cutting blade fixture 16 is released by loosening the locking knob 55, and the cutting fixture is moved along the mounting mandrels 30, 32 until the spacing between the cutting blade 18 and end of the spinal implant 14 approximately equals the distance between the arms 44, 46 of the caliper 42. The caliper arm 46 is placed on reference point 38, and the cutting fixture 16 is adjusted until spacing between the caliper arms and the reference marks is equal. The locking knob 55 is then tightened to lock the cutting fixture 16 and cutting blade 18 in place to cut the spinal implant 14 to the desired length. As shown in FIG. 7, a plurality of different reference points 40a, 40b, and 40c may be associated with the cutting fixture 16 to accommodate for different sized and shaped end caps for a spinal implant such as a corpectomy cage.

Figure 8:
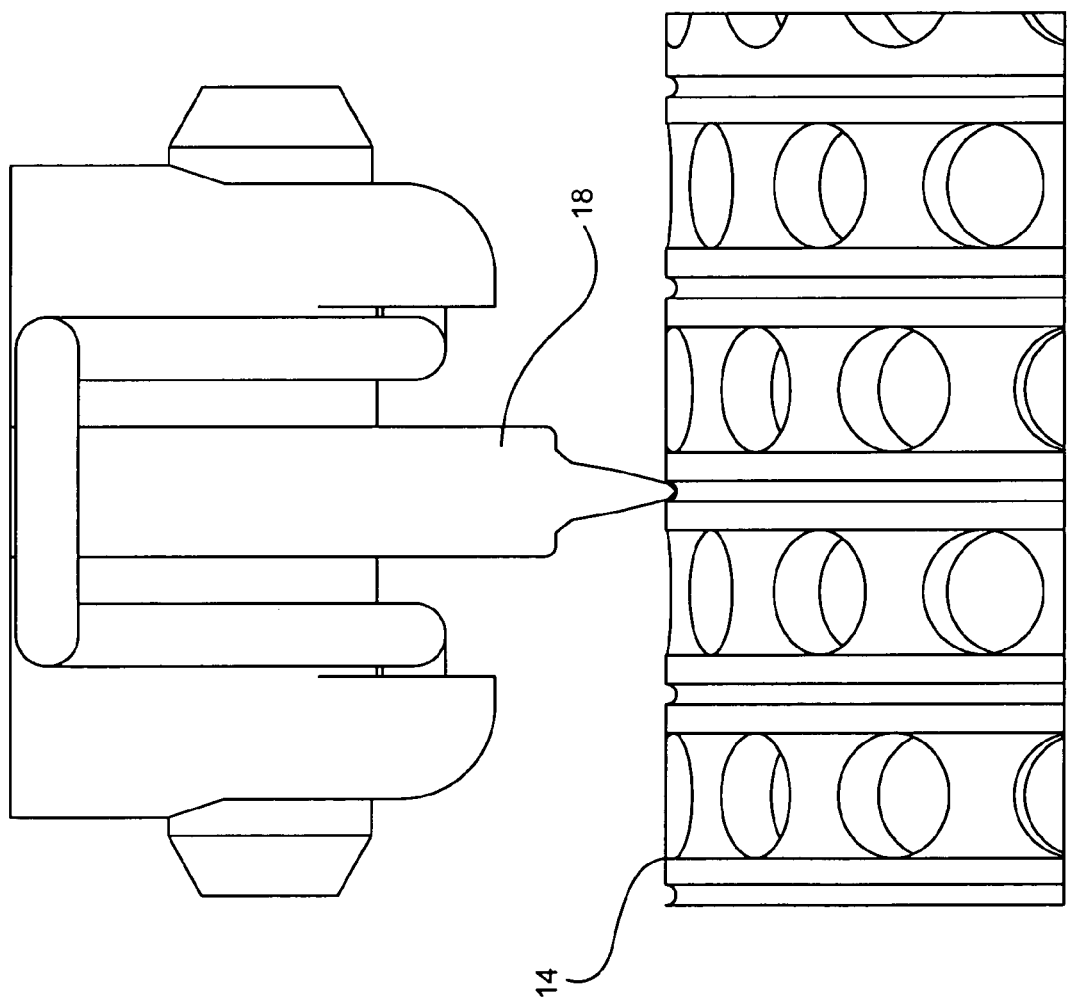
FIG. 8 is an enlarged partial perspective view showing a cutting blade in contact with a spinal implant according to one or more embodiments of the present invention.
Figure 10:
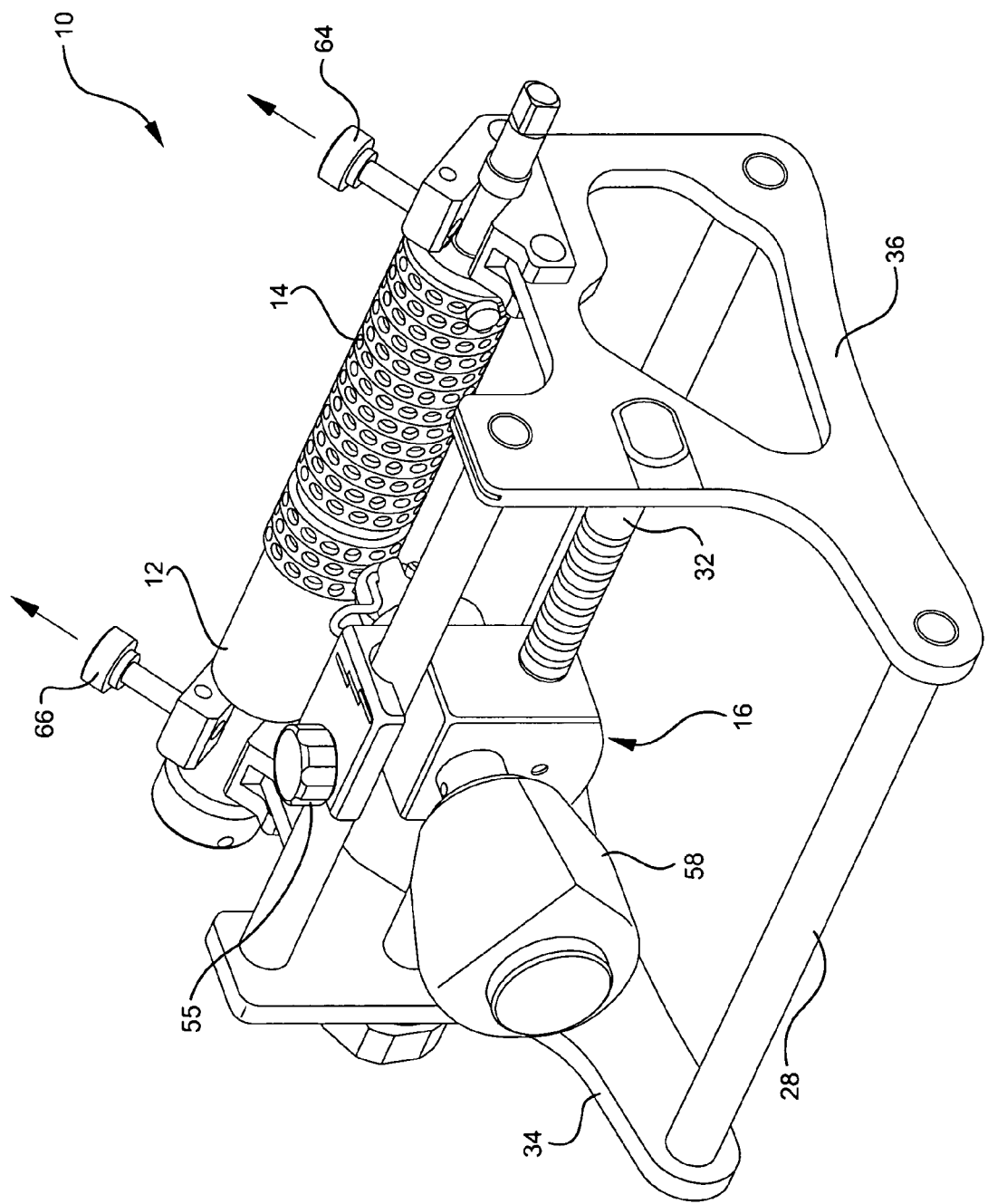
FIG. 10 is a perspective view showing the cutting apparatus after the spinal implant has been cut and prior to removal of the mandrel according to one or more embodiments.
Figure 11:
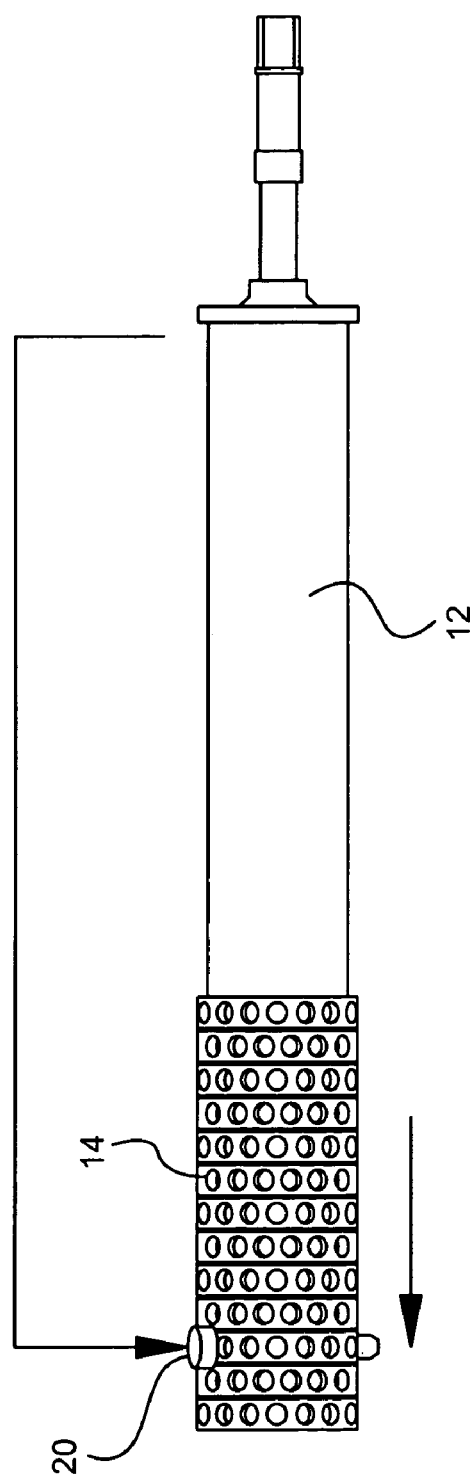
FIG. 11 is a perspective view showing removal of the spinal implant from the mandrel after the spinal implant has been cut according to one or more embodiments.
Figure 12:
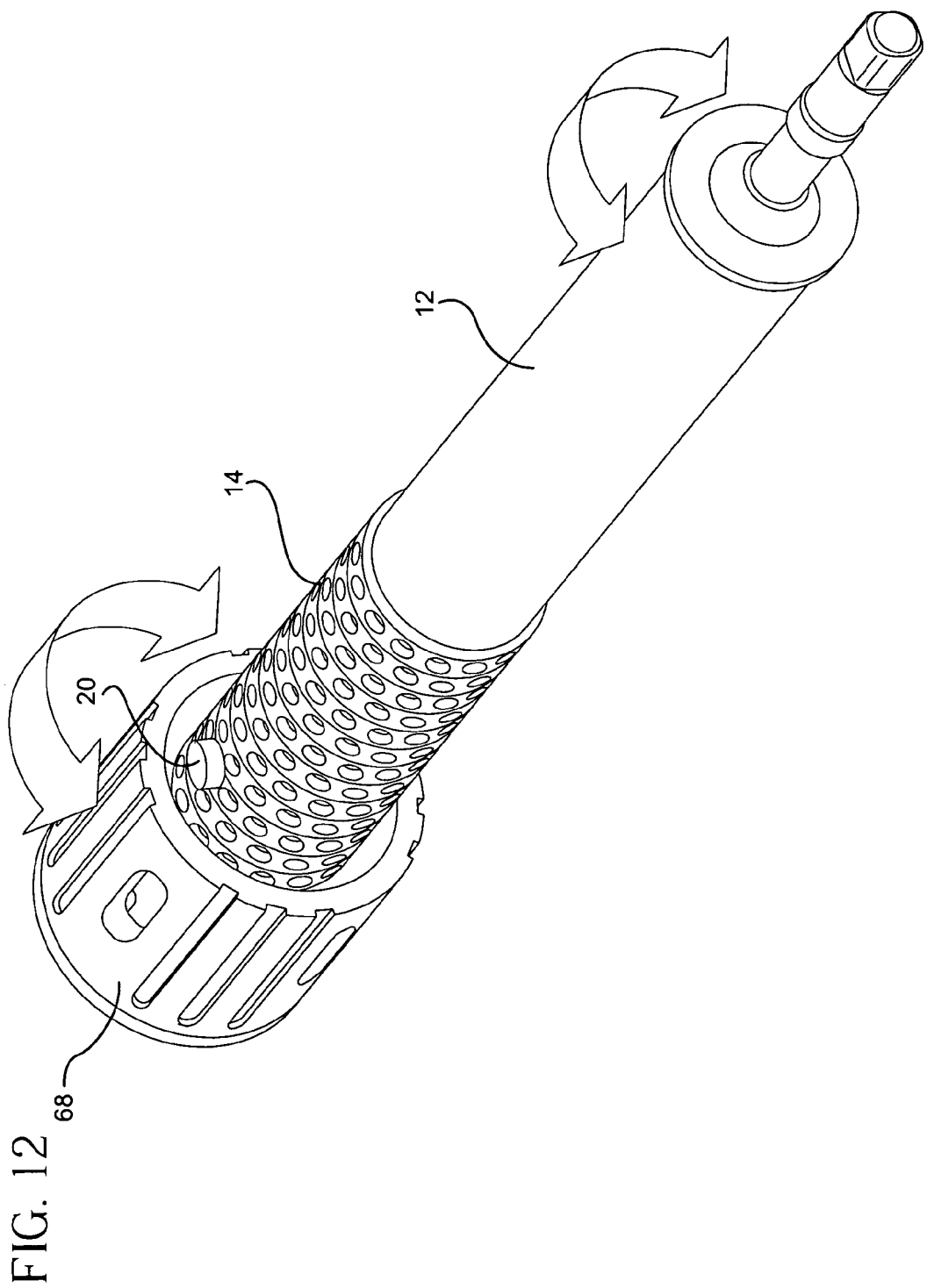
FIG. 12 is a perspective view showing the cut spinal implant being processed after cutting and prior to implantation according to one or more embodiments.

After the cutting blade fixture 16 and cutting blade 18 are locked in place with respect to the length of the cage, the adjustment knob 58 is rotated to move the blade towards the spinal implant until the cutting blade 18 is in contact with the spinal implant 14 as shown in FIG. 8. As shown in FIG. 9, the first mandrel 12 is then rotated by moving the handle 22 in a back and forth motion until the cutting blade 18 cuts through the spinal implant. Referring now to FIG. 10, the thumbscrews 64, 66 are loosened, and the mandrel 12 is removed from the apparatus. As shown in FIG. 11, the cut spinal implant 14 is then separated, and as shown in FIG. 12, the cut end of the implant 14 is processed with a burr removing device 68 to remove any burrs at the end of the spinal implant 14. The implant 14 that has now been accurately cut to size is then inserted in between two vertebrae using procedures known in the art. End caps (not shown) are typically attached to the ends of the corpectomy cage to assist implantation of the cage in between two vertebral bodies.

Although the invention herein has been described with reference to particular embodiments, it is to be understood that these embodiments are merely illustrative of the principles and applications of the present invention. For example, while the cutting blade shown in the preferred embodiments discussed herein is circular, it will be understood that other types of cutting blades can be used. For example, a straight cutting blade can be placed in fixed relation to the rotating mandrel, or a reciprocating blade could be used to cut the spinal implant. It is therefore to be understood that numerous modifications may be made to the illustrative embodiments and that other arrangements may be devised without departing from the spirit and scope of the present invention as defined by the appended claims and their equivalents.

The invention claimed is:

1. A spinal implant cutting apparatus comprising:
   a first mandrel configured to support a substantially cylindrical spinal implant;
   a cutting blade moveable from a first position at which it is spaced from a spinal implant supported on the first mandrel to a second position at which it is in cutting engagement with the spinal implant; and
   a pair of channels formed on opposite ends of the apparatus for receiving the first mandrel such that the first mandrel is detachable from the apparatus to permit loading and removal of the spinal implant on the first mandrel, the channels being made from a friction-reducing material.

2. The apparatus of claim 1, wherein the spinal implant is configured to be rotated with respect to the cutting blade.

3. The apparatus of claim 2, wherein the first mandrel is configured to support a hollow spinal implant such that the spinal implant is slidably mounted on the first mandrel.

4. The apparatus of claim 2, further comprising means for rotating the first mandrel.

5. The apparatus of claim 2, further comprising a handle associated with the first mandrel configured to rotate the first mandrel.

6. The apparatus of claim 5, further comprising a ratchet mechanism associated with the handle for rotating the first mandrel.

7. The apparatus of claim 2, further comprising a frame, the cutting fixture being slidably mounted to the frame.

8. The apparatus of claim 7, further comprising a first reference point associated with the frame and a second reference point associated with the cutting blade, the reference points configured to permit placement of the cutting blade such that the spinal implant can be cut to a desired length.

9. The apparatus of claim 8, wherein the reference points comprise a pair of notches configured to receive ends of an intervertebral caliper measurement device.

10. The apparatus of claim 8, further comprising a plurality of notches associated with the cutting blade referenced to a plurality of different sized spinal implants.

11. The apparatus of claim 2, further comprising a cutting fixture for securing the cutting blade, wherein the cutting blade is readily removable from the cutting fixture.

12. The apparatus of claim 2, wherein the cutting blade is configured to be positioned at a plurality of positions along the length of the spinal implant.

13. The apparatus of claim 11, wherein the cutting fixture is mounted on a frame configured to permit the cutting blade to move in increments with respect to the spinal fixture.

14. The apparatus of claim 13, wherein the increments are matched to marked spacings associated with spinal implant.

15. The apparatus of claim 11, wherein the cutting blade is held in place by a locking spring.

16. The apparatus of claim 11, wherein the cutting blade fixture is movable in a direction substantially transverse to the longitudinal axis of the spinal implant.

17. The apparatus of claim 16, wherein rotation of an adjustment knob causes movement of the cutting blade substantially transverse to the longitudinal axis of the spinal implant.

18. A spinal implant cutting apparatus comprising:
a frame including a rotatable first mandrel for supporting a substantially cylindrical spinal implant;
a cutting fixture including a cutting blade, the cutting fixture being slidably mounted to the frame such that the cutting fixture can be moved to a plurality of positions along the length of the spinal implant and cut the spinal implant to a pre-selected length; and
a pair of channels located on opposite ends of the frame for receiving the first mandrel such that the first mandrel is detachable from the apparatus to permit loading and removal of the spinal implant on the first mandrel, the channels being made from a friction-reducing material.

19. The cutting apparatus of claim 18, further comprising indicia associated with the apparatus for receiving an intervertebral space measurement to accurately determine the length of the spinal implant.

20. The cutting apparatus of claim 19, wherein the indicia comprises a pair of reference marks.

21. The cutting apparatus of claim 20, wherein the pair of reference marks are configured to received the ends of a caliper.

22. The cutting apparatus of claim 21, wherein the reference marks are associated with the cutting fixture and the frame.

23. The apparatus of claim 20, wherein the spinal implant includes a substantially tubular cage.

24. A spinal implant cutting apparatus comprising:
a first mandrel removably disposed within a pair of channels formed on opposite ends of a frame, the channels being made from a friction-reducing material, the removable mandrel adapted to receive a substantially tubular spinal implant;
a cutting blade configured to be placed in cutting engagement with the spinal implant; and
reference marks associated with the cutting blade and the apparatus adapted to receive an intervertebral spacing measurement from a caliper.

25. A spinal implant cutting apparatus comprising:
a first mandrel configured to support a substantially cylindrical spinal implant;
a cutting blade moveable from a first position at which it is spaced from a spinal implant supported on the first mandrel to a second position at which it is in cutting engagement with the spinal implant;
a handle associated with the first mandrel configured to rotate the first mandrel;
wherein the spinal implant is configured to be rotated with respect to the cutting blade.

26. The apparatus of claim 25, further comprising a ratchet mechanism associated with the handle for rotating the first mandrel.

27. A spinal implant cutting apparatus comprising:
a first mandrel configured to support a substantially cylindrical spinal implant;
a cutting blade moveable from a first position at which it is spaced from a spinal implant supported on the first mandrel to a second position at which it is in cutting engagement with the spinal implant;
a cutting fixture for securing the cutting blade, wherein the cutting blade is readily removable from the cutting fixture;
wherein the spinal implant is configured to be rotated with respect to the cutting blade, the cutting blade fixture is movable in a direction substantially transverse to the longitudinal axis of the spinal implant, rotation of an adjustment knob causes movement of the cutting blade substantially transverse to the longitudinal axis of the spinal implant, and the mandrel is mounted in a pair of channels formed on the apparatus, the channels being made from a friction-reducing material.

28. The apparatus of claim 1, further comprising a thumb screw for holding the mandrel in at least one of the channels.

29. The apparatus of claim 28, wherein the apparatus includes a thumbscrew associated with each channel.

30. The cutting apparatus of claim 18, further comprising a thumb screw for holding the mandrel in at least one of the channels.

31. The cutting apparatus of claim 30, wherein the apparatus includes a thumbscrew associated with each channel.

32. The apparatus of claim 24, further comprising a thumb screw for holding the mandrel in at least one of the channels.

33. The apparatus of claim 32, wherein the apparatus includes a thumbscrew associated with each channel.

* * * * *